United States Patent [19]

Bergner et al.

[11] 4,203,812
[45] May 20, 1980

[54] PROCESS FOR PREPARING BASIC ALUMINUM CHLORIDES

[75] Inventors: Dieter Bergner, Kelkheim; Max Danner, Gersthofen, both of Fed. Rep. of Germany

[73] Assignee: Hoechst Aktiengesellschaft, Frankfurt am Main, Fed. Rep. of Germany

[21] Appl. No.: 889,334

[22] Filed: Mar. 23, 1978

[30] Foreign Application Priority Data

Mar. 25, 1977 [DE] Fed. Rep. of Germany ....... 2713236

[51] Int. Cl.$^2$ .................. C25B 1/26; C25B 11/10
[52] U.S. Cl. .................... 204/94; 204/290 F
[58] Field of Search .................. 204/94, 290 F

[56] References Cited

U.S. PATENT DOCUMENTS

| | | | |
|---|---|---|---|
| 2,945,791 | 7/1960 | Gibson | 204/98 |
| 3,113,911 | 12/1963 | Jones | 204/94 |
| 3,240,687 | 3/1966 | Konig et al. | 204/94 |
| 4,005,003 | 1/1977 | Popplewell et al. | 204/290 F |
| 4,039,400 | 8/1977 | Hayfield | 204/290 F |

*Primary Examiner*—G. Kaplan
*Attorney, Agent, or Firm*—Connolly and Hutz

[57] ABSTRACT

When aqueous solutions of aluminum chloride or of basic aluminum chloride having the formula $Al_2(OH)_mCl_{6-m}$ wherein m is a number from 0 to 5.3 are submitted to electrolysis chlorine is removed and the Al/Cl ratio of the solution increases. The electrolysis is performed without diaphragm. Graphite anodes cannot be used. It is possible to process the resulting solutions to solid basic aluminum chloride having the formula $Al_2(OH)_nCl_{6-n}$ wherein n is a number from 1 to 5.34.

6 Claims, No Drawings

PROCESS FOR PREPARING BASIC ALUMINUM CHLORIDES

Basic aluminum chlorides are more and more used in various fields. They are used, for example, as active ingredients in cosmetic preparations such as antiperspiration agents, or in hemostatic substances. They are also used for hydrophobizing textile materials, as tanning agents and as flocculants for water treatment. Recently, basic aluminum chlorides are also used as starting materials for preparing refractory substances, inorganic fibers and catalysts on aluminum oxide basis.

The processes used for obtaining basic aluminum chlorides may be divided roughly in two groups.

The first group includes all processes which lead to the desired compounds by purely chemical methods, for example by double conversion of other basic aluminum salts, by partial hydrolysis of anhydrous aluminum chloride, by thermal splitoff of hydrogen chloride from aluminum chloride-hexahydrate or by reaction of aluminum hydroxides, which are capable of reaction and which may optionally be obtained from aluminum oxides or aluminum oxide-hydrates by decompositions or precipitations, with hydrochloric acid or aluminum chloride (German Offenlegungsschrift No. 1,567,470, German Auslegeschrift Nos. 2,309,610, 1,102,713 and 1,041,933).

The basic aluminum chlorides may also be obtained by using ions exchangers (German Offenlegungsschrift No. 2,518,414).

The second group includes the electrochemical processes which start in some cases from plates of metallic aluminum which are dissolved in hydrochloric acid under the action of electric current (German Pat. No. 1,174,751). The disadvantages of this process resides in the fact that the raw material is quite expensive. More interesting from the economical standpoint are, therefore, electrochemical processes submitting to electrolysis aqueous aluminum solutions, that may be prepared from cheap and easily accessible raw materials or that are on sale at low prices as waste solutions.

The process according to German Auslegeschrift No. 1,204,207 is operating in such a way that the aluminum chloride solution is used as catholyte in a cell composed of three chambers separated from one another by means of ions exchanger membranes. Sulfuric acid is used as anolyte. The third chamber is situated between the cathode chamber and the anode chamber; this third chamber contains aluminum chloride solution, too; its concentration has to be kept constant by continuously adding fresh aluminum hydroxide. This process implies the inconvenience of enormous technical expenditure and effort, as well for the construction of the cells as during operation.

A process described in German Pat. No. 734,503 is working in a similar way, which comprises electrolyzing aluminum chloride solutions between graphite electrodes with the use of a diaphragm, yielding in the cathode chamber basic aluminum chloride, while chlorine is obtained at the anode. However, this process does not satisfy either, since obviously carbon spreads from the anode into the anolyte in a way not clearly understood and reaches the cathode—after diffusion of the anolyte by the diaphragm; the said carbon separates there as very finely divided, resulting in a contaminated basic aluminum chloride having a more or less grey color shade.

Corresponding results are obtained according to processes described in German Offenlegungsschrift No. 2,310,073 and in Japanese Pat. No. 73 31 838, if graphite electrodes are used, with the use of a diaphragm. The first of the afore mentioned literature specifications warns against operating without diaphragm, since a shifted pH in the anode area may lead to a diminution of the current yield and to a modification of the composition of the basic aluminum chloride, due to the formation of chlorine oxides, so that the basic aluminum chlorides would finally contain intolerable quantities of chlorate. As shown by experiments of our own, a process without diaphragms would yield totally black products, if graphite anodes are used. Both literature specifications state that the starting material has to be low-basic aluminum chloride; the Japanese Patent states as the reason that the use of aluminum chloride solutions leads to a corrosion of the diaphragm material, due to their high degree of acidity (pH less than 0.1) and to troubles with the electrolysis.

The present invention is aimed now at providing a process for preparing basic aluminum chlorides by way of electrolysis without the use of a diaphragm and starting not only from low-basic aluminum chloride, but directly from aluminum chloride solutions, which process avoids however the afore described disadvantages.

This process for preparing aqueous solutions of basic aluminum chloride of the general formula $Al_2(OH)_nCl_z$, wherein n is a number from 1 to 5.3 and z is a number from 5 to 0.66 and wherein the sum of $n+z$ is always 6, by electrolysis of an aqueous solution of aluminum chloride or of a basic aluminum chloride of lower basicity, at temperatures of from 50° to 120° C. and current densities of from 200 to 4000 A/m$^2$, which process comprises subjecting the said aluminum salt solutions, between a cathode of graphite or of a platinum metal or of a material coated with a platinum metal and an anode the body of which consists of a titanium alloy or titanium and is prepared partially or entirely with metals of the platinum group and/or oxides thereof, optionally in admixture with titanium oxides, without the use of a diaphragm, to electrolysis until a basic chloride of the desired stoichiometric composition has formed.

It was surprising and could not be expected that the process according to the present invention can be applied successfully in electroylzing aluminum chloride solutions using preferably graphite cathodes and anodes of titanium treated with platinum metals and/or platinum metal oxides, without using a diaphragm. This holds because the state of the art maintained prejudices against such a processing method, based on the low pH values at the beginning of the elctrolysis and the elevated pH at the end of this electrolysis, and based on the extremely low content of chloride ions in the electrolyte during the process, so that such a processing method was considered to be unpromising. Moreover, it had to be reckoned with the electrode material not being able to resist to a pH range from about 0 to 4, a range which is always involved during the electrolysis, since electrodes are used that are designed for the use within a smaller pH range, such as it occurs usually in the chlorine-alkaline-electrolysis. It was neither to be expected that the removal of heavy metals (having penetrated into the electrolyte via the starting products) at the cathode, i.e. the purification of the basic aluminum chloride solution during the electrolysis by means of mixing catholyte and anolyte, is not jeopardized and that no formation of chlorate occurs at all, this latter fact having a favorable effect also on the current efficiency. Other advantage are also, set aside the economy on diaphragm material, the very simple construction of the electrolysis cell and the small surface needed for the disposition of the electrodes, thus improving essentially the space/time yield of the cell as compared to the yield achieved in a cell with diaphragm. Another advantageous result is that the voltage is lower by about 0.5 volt compared with the diaphragm process. This corresponds to a remarkable energy again.

Moreover, the processing method without diaphragm leads to very uniform products, for the formation of gas around the electrodes guarantees a constant and thorough mixing and thus homogeneity of the whole electrolyte.

The preferred starting material for the process of the invention to prepare aqueous solutions of basic aluminum chlorides is common aluminum chloride that may be obtained by known processes, e.g. by dissolving aluminum hydroxides or aluminum oxides in hydrochloric acid. However, it is also possible, of course, to start from basic aluminum chlorides with a basicity inferior to the desired degree. Such basic aluminum chlorides of lower basicity have the empirical composition of $Al_2(OH)_mCl_{6-m}$, m representing a number from 5.3 to zero, m being smaller than n (in the formula of the final product). The concentration of the aluminum salt solution may be chosen deliberately,, the operation with solutions saturated while cold is, however, advantageous, containing about 50 weight % of aluminum chloride, when these latter are used.

A preferred material for the cathodes is graphite, but the use of platinum metals or of materials coated with platinum metals, e.g. platinum-plated refined steel, is also possible. Optionally there may also be used directly other metals, such as refined steels, if care is taken that all cathode parts not covered by the electrolyte, are protected against corrosion and that the cell is constantly under current. The electrodes mentioned in the last place, may also be coated e.g. with very finely divided platinum metals, in order to reduce the overvoltage for hydrogen.

The chlorine-resistant anodes used for the process of the invention may not be prepared of graphite, but of a series of different materials, for example lead dioxide or of materials coated with lead dioxide. But in general the chlorine-resistant anodes consist of a core of an electrolytic film-forming metal carrying a coating.

In this respect are to be understood by electrolytic film forming metals ("valve metals") titanium, zircon, tantalum, molybdenum and wolfram. Preference is given to cores consisting of titanium or of a titanium alloy such as Pd-stabilized titanium. The core may be prepared e.g. of sintered titanium. In that case, the coating may be applied advantageously by impregnation with a solution or suspension containing at least one platinum metal compound and subsequent thermal after-treatment.

Even if the core does not consist of titanium, a coating that contains at least one metal of the platinum group, e.g. Pt, Ru, Ir, Rh or at least one oxide of a metal of the platinum group, is an advantage. The coating may as well consist of a metal of the platinum group. There may also be used electrodes, the coating of which is composed of two layers, the inner layer (primer, adjacent to the core) consisting of titanium oxides of formula $TiO_x$ (with $1.7 \leq x \leq 1.999$ and the layer weight of 50 to 6.000 g/m²) and an outer layer containing at least one metal of the platinum group or at least one oxide of a metal of the platinum group.

There may also be used coatings that consist of a mixture containing at least one metal of the platinum group or at least an oxide of a metal of the platinum group and, as well, at least an oxide of an electrolytic film-forming metal. As oxide of an electrolytic film-forming metal is preferably used titanium oxide.

The electrode body may have the shape of e.g. plates, sheets, perforated plates, grids or nets.

The electrolysis is carried out at temperatures of from 50 to 120, preferably from 60° to 80° C. The current density that is limited by the formation of foam at the electrodes only, may amount to up to 4000 A/m², and the cell voltage varies from 2 to 8, preferably from 3 to 4.5 volt. The spaceing from one electrode to the next may be very small; it is thus possible to approach the electrodes till a few millimeters of interspace only.

The mixture of hydrogen and chlorine that is formed during the electrolysis, may be introduced into sodium hydroxide solution, for example after dilution with air below the explosion limit, bleaching liquor being formed from chlorine. The residual gases free from chlorine may then be emitted.

The aqueous solutions of the basic aluminum chlorides obtained according to the invention still contain small amounts of dissolved chlorine that may be discharged for example by blowing out or by evaporation, or that may be removed in an especially simple manner by brief contact with aluminum chips. It is then possible to isolate from the aqueous solutions, in known manner, colorless aluminum chlorides, which, when dissolved in water form again clear solutions.

The process of the invention is not limited to the preparation of basic aluminum chlorides with an aluminum/chlorineatomic ratio of the range of 2:1, there may further be obtained basic chlorides up to an Al/Cl-atomic ratio of 3:1, though the current efficiency decreases in the latter case.

The following Examples illustrate the process of the invention and show the improvement as compared with processes known to the art.

EXAMPLE 1

400 g of an aqueous solution, saturated with aluminum chloride-hexahydrate are charged in a trough of plastic materials (volume: 410 cm³). The solution contains 6.1 weight % of aluminum and 24.6 weight % of chloride. Electrolysis is carried out at about 70° C. with the use of graphite cathode and of a titanium anode coated with ruthenium oxide/titanium oxide having each an active surface of 70 cm²; the cell voltage during the electrolysis varies from 3 to 4 V at a maximum current density of 800 A/m².

A total of 150 g of the starting solution is introduced additionally into the cell during the electrolysis, in order to compensate the electrolyte loss that occurs by water evaporation.

After an electrolysis period of 22 hours and after a charge throughput of 94 Ampere/hour, at a current efficiency of 92%, there are obtained 440 g of a solution containing 7.6 weight % of aluminum and 4.8 weight % of chloride, corresponding to an atomic ratio of aluminum:chloride of 2.09:1. The solution is treated with aluminum chips for about two hours, in order to remove the dissolved chlorine. The solution is free of chlorate, colorless and clear.

EXAMPLE 2

The electrolysis is carried out as described in Example 1. A basic aluminum chloride solution containing 7.8 weight % of aluminum and 23.3 weight % of chloride, corresponding to an atomic ratio of aluminum:chlorine of 0.44:1, is used instead of the aluminum chloride-hexahydrate solution. As electrodes are used graphite (cathode) and titanium coated with platinum/iridium oxide (anode).

From 600 g of starting solution result, after 16 hours at 70° C., a cell voltage of from 3 to 4.5 V and a max. current density of 1.400 A/m$^2$, 450 g of a solution containing 10.4 weight % of aluminum and 6.9 weight % chloride of 1.97:1, a current efficiency of 92% at a charge throughput of 89 A per hour. The solution is clear, colorless and free of chlorate.

EXAMPLE 3: (Comparison according to the state of the art)

The electrolysis is carried out as described in Example 1, i.e. without diaphragm, but with the use of a graphite cathode and a graphite anode.

After 34 hours at 70° C., a cell voltage of 3 to 4 V and a maximum current density of 730° A/m$^2$ there are obtained, from 550 g of starting solution, 430 g of a solution containing 7.8 weight % of aluminum and 4.8 weight % of chloride, corresponding to an atomic ratio of aluminum:chloride of 2.12:1. The current efficiency is 83% at a charge throughput of 104 A per hour. The solution is darkbrown and contains 0.5 weight % of chlorate. No discoloration is possible neither by centrifugation nor by filtration or by applying an adsorption agent.

EXAMPLE 4: (Comparison according to the state of the art)

In a beaker of 600 cm$^3$ a cylinder-shaped bag made of PVC fabric (volume 180 cm$^3$) is fitted in hanging position as anode space. This diaphragm bag is charged with 200 g of an aqueous aluminum hexahydrate solution saturated while cold, having the composition specified in Example 1 as anolyte, and with 258 g of the same solution in the cathode space (outside the diaphragm). Electrolysis takes place with graphite electrodes.

260 g of a catholyte, containing 7.5 weight % of aluminum and 5.=weight % of chloride, corresponding to an atomic ratio of aluminum:chloride of 1.97:1, having a current efficiency of 92% at a charge throughput of 58 A per hour, are obtained after 24 hours at 70° C., a cell voltage of 4 V and a maximum current density of 370 A/m$^2$. The solution is free of chlorate, but slightly turbid and has a grey color shade.

After termination of the electrolysis the anolyte (200 g) contains 14.4 weight % of chloride and 4.1 weight % of aluminum corresponding to aluminum:chloride of 0.38:1.

EXAMPLE 5

489 g of a basic aluminum chloride solution are used, containing 7.4 weight % of aluminum and 23.4 weight % of chloride, corresponding to an atomic ratio of aluminum:chloride of 0.42:1. As anode is used titanium coated with ruthenium oxide/titanium oxide and as cathode is used platinum.

After a period of 14.5 hours at 75° C., a cell voltage of 3.5 to 4.5 V and a maximum current density of 1.200 A/m$^2$, there are obtained 420 g of a solution containing 8.5 weight % of aluminum and 5.2 weight % of chloride, corresponding to an atomic ratio of aluminum:chloride of 2.16:1. The current efficiency is 91% at a charge throughput of 77 Amperes per hour. Nor formation of chlorates occured.

EXAMPLE 6

597 g of the aluminum salt solution of Example 2 are electrolyzed with the use of a graphite cathode and of an anode of titanium coated with platinum. During the electrolysis the cell voltage amounts to 3.5–4.5 V, at a temperature of 70° C. and a maximum current density of 1,200 A/m$^2$. After an electrolysis period of 15 hours and a charge throughput of 89 Amperes per hour at a current efficiency of 89%, there are obtained 445 g of a solution containing 10.4 weight % of aluminum and 7.6 weight % of chloride, corresponding to an atomic ratio of aluminum:chloride of 1.80:1. The solution is clear, colorless and free of chlorate.

What is claimed is:

1. A process for preparing aqueous solutions of basic aluminum chloride of the formula Al$_2$ (OH)$_n$Cl$_z$, wherein n is a number from 1 to 5.3 and z is a number from 5 to 0.66 and the sum of n+z is always 6, by electrolysis of an aqueous solution of aluminium chloride or of a basic aluminium chloride of lower basicity, at temperatures of from 50° to 120° C. and current densities of from 200 to 4000 A/M$^2$, which process comprises subjecting the said aluminium salt solutions between a cathode of graphite, of a platinum metal, or of a material coated with a platinum metal, and an anode having a core of titanium or a titanium alloy and a coating on said core of at least one metal of the platinum group, of at least one oxide of a metal of the platinum group, or of a mixture thereof, without the use of a diaphragm, to electrolysis until a basic chloride of the desired stoichiometric composition has formed.

2. A process as claimed in claim 1, wherein the coating of the anode is of at least one metal of the platinum group and of at least one oxide of a metal of the platinum group.

3. A process as claimed in any one of claims 1 or 2, wherein the coating of the anode includes additionally at least one titanium oxide.

4. A process as claimed in claim 1, wherein the coating of the anode comprises an inner layer of titanium oxide of the formula TiO$_x$ wherein x is 1.7–1.999 having the layer weight of 50–6.000 g/m$^2$ and an outer layer comprising at least one metal of the platinum group, or at least one oxide of a metal of the platinum group.

5. A process as claimed in claim 1, wherein the core of the anode comprises sintered titanium.

6. A process as claimed in claim 5, wherein the core of the anode is coated by impregnating the core with a solution or suspension of at least one platinum metal compound, and by subsequent thermal treatment.

* * * * *